United States Patent [19]

Sainz et al.

[11] 4,391,148

[45] Jul. 5, 1983

[54] METHODS AND APPARATUS FOR MEASURING THE CROSS-SECTIONAL AREA OF A DUCT AND THE VOLUME FLOW RATE OF FLUID IN THE DUCT

[75] Inventors: Antonio J. Sainz; Victor C. Roberts, both of London, England

[73] Assignee: National Research Development Corporation, London, England

[21] Appl. No.: 238,952

[22] Filed: Feb. 27, 1981

[30] Foreign Application Priority Data

Feb. 29, 1980 [GB] United Kingdom ................. 8007008
Jun. 11, 1980 [GB] United Kingdom ................. 8019049

[51] Int. Cl.$^3$ .......................... A61B 5/10; G01F 1/66
[52] U.S. Cl. .................................. 73/861.25; 73/227; 128/663
[58] Field of Search .................... 73/861.25, 602, 227; 128/663; 367/90; 364/564

[56] References Cited

U.S. PATENT DOCUMENTS

| | | | |
|---|---|---|---|
| 3,554,030 | 1/1971 | Peronneau | 73/861.25 |
| 3,675,192 | 7/1972 | Fahrbach | |
| 4,095,597 | 6/1978 | Hassler | 73/602 X |
| 4,103,679 | 8/1978 | Aronson | |

OTHER PUBLICATIONS

NASA Progress Report, NRG 33010074, Cornell University, 1969, "Directional Doppler Flowmeter", McLeod, R. D.
"Ultrasound in Medicine and Biology", 2, 1, Accuracy and Limitations of the Ultrasonic Doppler Blood Velocimeter and Zero Crossing Detector, by Lunt, M. J., 1975.
"Ultrasonic Doppler Velocimetry", Chapter 7, by Roberts and Sainz, of the Book Non-Invasive Physiological Measurements, Edited by Rolfe, Academic Press, 1979, p. 164, Paragraph 3.5.
"Phase Locked Loop Techniques Applied to Ultrasonic Doppler System Processing", Sainz et al., Ultrasonics 14, pp. 128 to 132, May 1976.
"Vessel Area Detection with C. W. Ultrasound", Sainz and Roberts, Medical and Biological Engineering, Mar. 1976, pp. 245 and 246.
Chapter 27, "Initial Evaluation of Transcutaneous Aortovelography-A New Non-Invasive Technique for Haemodynamic Measurements in the Major Thoracic Vessels", by Light, pp. 325 to 360 of the Book Cardiovasculaor Applications of Ultrasound, Edited by Reneman, R. S., North Holland Publishing Co.

Primary Examiner—Charles A. Ruehl
Attorney, Agent, or Firm—Cushman, Darby & Cushman

[57] ABSTRACT

The invention is particularly related to the measurement of the area of a blood vessel and the volume flow rate of blood in such vessels. An ultrasonic Doppler velocimeter which derives a number of velocity signals dependent on the number of different velocities in a duct is coupled by way of a limiter to a frequency-to-voltage converter which therefore has an output with one component for each velocity signal. A further frequency-to-voltage converter provides a signal dependent on the number of velocity signals and since this number depends on the duct area, the output from the further converter is a measure of this area. By using another frequency-to-voltage converter and a mean detector, a mean velocity signal is obtained which when multiplied by the area signal generates volume flow rate.

9 Claims, 2 Drawing Figures

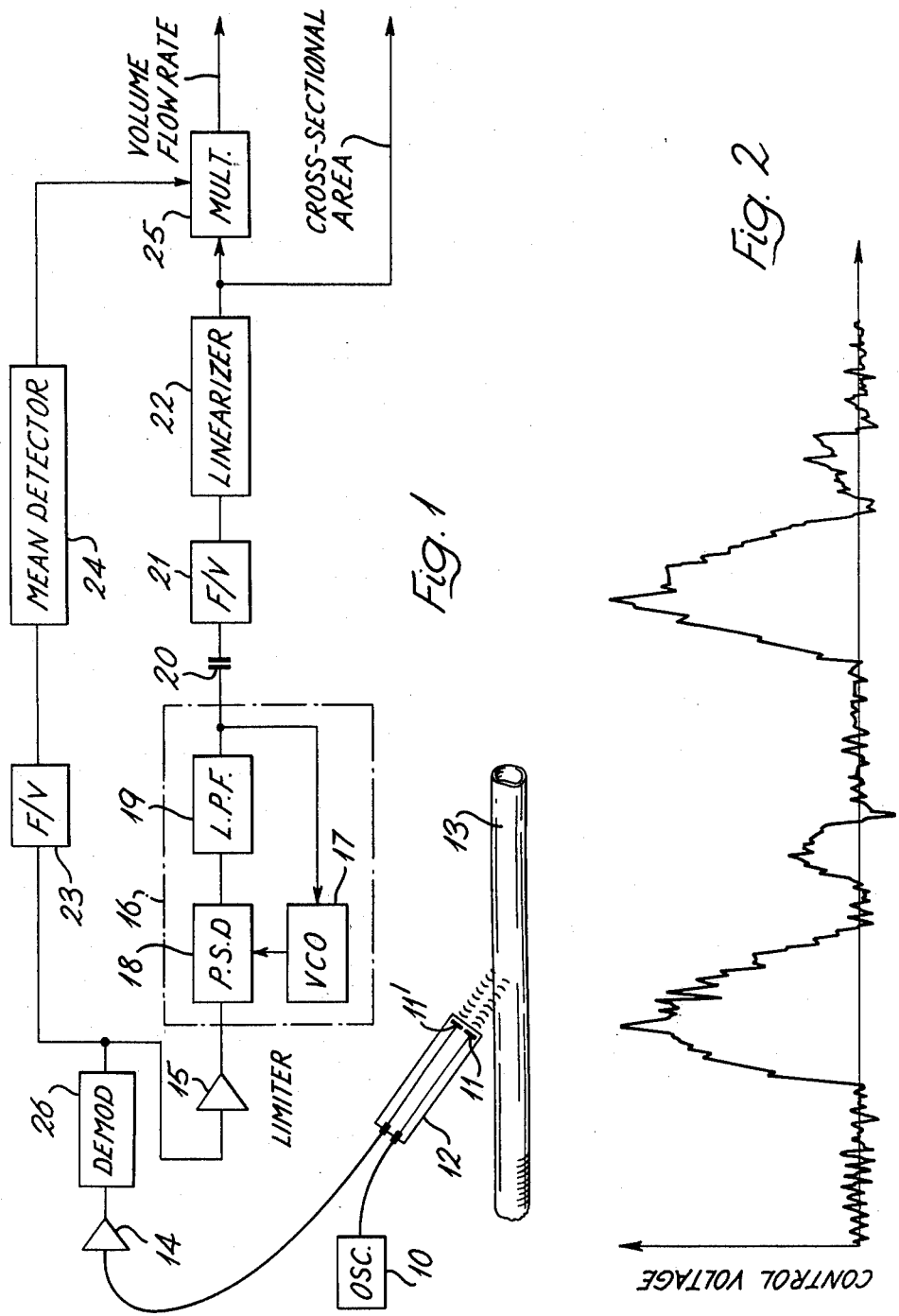

METHODS AND APPARATUS FOR MEASURING THE CROSS-SECTIONAL AREA OF A DUCT AND THE VOLUME FLOW RATE OF FLUID IN THE DUCT

The present invention relates to apparatus and methods for measuring the cross-sectional area of a duct, particularly but not exclusively the cross-sectional area of a blood vessel. The invention also concerns apparatus and methods for measuring volume flow rate in ducts.

It is known to measure the velocity of blood in blood vessels by using a Doppler velocimeter. Such velocimeters are described, for example, in NASA Progress Report NRG 33010074, Cornell University, 1969 "Directional Doppler Flowmeter" McLeod, R. D.; in "Ultrasound in Medicine and Biology", 2, 1, "Accuracy and Limitations of the Ultrasonic Doppler Blood Velocimeter and Zero Crossing Detector" by Lunt, M. J. (1975); and in the book "Non-Invasive Physiological Measurements" edited by Rolfe, Academic Press, 1979, Chapter 7 "Ultrasonic Doppler Velocimetry" by Roberts and Sainz.

The measurement of blood vessel calibre or cross-sectional area is important in making, on-line, non-invasive measurements of volume flow rate and blood vessel wall elasticity (by relating pressure changes to dimension changes). Both these quantities are of prime importance in the assessment of the degree of atheromatous involvement in an artery. Furthermore, a knowledge of vessel calibre permits the measurement of cardiac output without the need for recourse to general approximations and aortography.

According to a first aspect of the present invention there is provided apparatus for measuring the cross-sectional area of a duct containing a fluid, comprising means for deriving a plurality of velocity signals, each corresponding to a respective velocity of fluid in a duct, and the number of velocity signals depending on the number of different velocities concurrently present in the duct, and analysis means for deriving an area signal representative of the number of velocity signals obtained.

Since the area signal represents the number of concurrent velocities it is also (as discussed in more detail below) representative of the cross-sectional area of the duct.

Advantages of the present invention include avoiding the need for general approximations in estimating the cross-sectional area of blood vessels or of surgery in measuring such cross-sections. The apparatus may be constructed in a form which is sensitive enough to provide a signal which shows the variation of blood vessel cross-section with cyclic blood pressure.

The means for deriving a plurality of velocity signals may comprise a known Doppler velocimetry apparatus including an oscillator coupled to an ultrasound transmission transducer, and an ultrasound transmission receiver which derives a plurality of signals each having a frequency dependent on a respective fluid velocity in the duct.

The analysis means may comprise means for deriving a spectrum signal having one component portion for each velocity signal, and means for deriving a signal representative of the number of component portions in the spectrum signal.

An amplitude limiter coupled to a first frequency-to-voltage converter (which may be a phase-locked loop) may form the means for deriving the spectrum signal, and the means for deriving a signal representative of the number of component portions in the spectrum signal may comprise a second frequency-to-voltage converter. Means may be provided between the two frequency-to-voltage converters for removing low frequency signals in the output of the first frequency-to-voltage converter deriving the spectrum signal.

Where the amplitude limiter and frequency-to-voltage converter have a combined characteristic which is non-linear, a linearizer circuit may be coupled to the output of the second frequency-to-voltage converter and where this converter employs a phase-locked loop the linearizer may be based on a square law characteristic.

The apparatus must be used in such a way that the duct or vessel is completely insonated (bathed in sound) while adjacent vessels are avoided. In addition the motion of fluid within the duct must always exceed the motion of surrounding objects such as body tissues.

Apparatus according to the invention may also include means for deriving a signal representative of mean fluid velocity in the duct and means for multiplying the area signal by the signal representative of mean velocity to provide a signal representative of volume flow rate. The means for deriving a signal representative of mean velocity may comprise a further frequency-to-voltage converter coupled to receive Doppler signals and a mean detector coupled to the output of the further converter.

According to a second aspect of the present invention there is provided a method of measuring the cross-sectional area of a duct containing a fluid, comprising the steps of deriving a plurality of velocity signals, each corresponding to a respective velocity of fluid in a duct and the number of signals depending on the number of different velocities concurrently present in the duct, and deriving an area signal representative of the number of velocity signals obtained.

The method may be extended to provide an output representative of volume flow rate by deriving a signal representative of mean velocity in the duct and by multiplying the signal so derived by the area signal.

Certain embodiments of the invention will now be described by way of example, with reference to the accompanying drawings, in which:

FIG. 1 is a block diagram of an embodiment of apparatus according to the invention, and FIG. 2 is a graph of variation with time of a control voltage present in the apparatus of FIG. 1.

In FIG. 1 an oscillator 10 typically operating at 5 MHz is coupled to a transmit crystal 11 in an ultrasonic probe 12. In operation the probe 12 is positioned so that ultrasound is transmitted as nearly as possible to insonate the whole of a blood vessel 13 whose cross-sectional area and volume-flow rate is to be measured, at an angle which is ideally not perpendicular to the longitudinal axis of the blood vessel. This configuration is to ensure that ultrasound emitted from the crystal 11 has a substantial component along the axis of the blood vessel 13.

Sound reflected from blood flowing in the vessel 13 is received by a receive crystal 11' which, due to the Doppler effect, generates an electrical signal having a spectrum of frequencies related to the different velocities of blood flowing in the vessel 13. The probe 12 and the oscillator 10 form the basis of the known ultrasonic Doppler velocity meter which is described in the publications mentioned above near the beginning of the specification.

After amplification in an amplifier 14, signals from the crystal 11' are passed to a demodulator 26 which has an output consisting of a large number of different frequencies each representative of a different velocity in the vessel 13. These signals are passed by way of an amplitude limiter 15 to a frequency-to-voltage converter 16 comprising a phase-locked loop (PLL). The PLL consists of a voltage-controlled oscillator (VCO) 17, a phase-sensitive detector 18 and a low pass filter 19. Phase-locked loops are, of course, well known and integrated circuits forming phase locked loops are available. For the present embodiment any of the Signetics integrated circuits Nt561 to 565 are suitable. These integrated circuits have external terminals for the connection of a capacitor which determines the characteristic of the low pass filter 19. However, in this application as a frequency to voltage converter, the low pass filter is required to have as wide a bandwidth as possible and for this reason no capacitor is connected across the above mentioned terminals.

A phase-locked loop generates a control voltage for its VCO 17 which is dependent on the difference in phase between the VCO output and the output of the limiter 15 and thus the control voltage represents the instantaneous frequency at the output of the limiter 15. In the presence of multiple frequencies the characteristic of the PLL causes the control voltage to dwell at a level corresponding to each applied frequency for a time which depends on the amplitude of each applied frequency. Since the object of using the PLL 16 is to provide a signal having a distinct output or component for each Doppler frequency received and therefore for each velocity in the blood vessel 13, the control voltage is required to dwell for the same time for each frequency regardless of the amplitude of the signal conveying that frequency. The limiter 15 is therefore provided to ensure that all Doppler signals reaching the PLL 16 have the same amplitude. This ensures that within the operational range, the PLL is sensitive only to the phase and not the amplitude of the Doppler signals. As received by the crystal 11' amplitudes depend on distance of the particle in the bloodstream having a particular velocity; for example signals due to velocities near the probe 12 have considerably higher amplitudes than those due to velocities on the far side of the vessel 13 from the probe.

In this method of measuring cross-section it is assumed that every elemental area of cross-section passes blood at a different velocity and this is not an unrealistic assumption because although velocities around an annulus in the cross-sectional area of the vessel 13 have the same nominal velocity their phases are different. Of course, the number of velocities detected depends on the resolution of the PLL 16 but by using the limiter 15 this resolution achieves a suitable value.

FIG. 2 is an approximate sketch of the type of signal obtained at the output of the PLL 16. The magnitude of the control voltage at any instant is representative of the frequency at the output of the limiter 15 and therefore of the velocity corresponding to that frequency of blood in the vessel 13. Thus each maximum and each minimum in FIG. 2 of which there are many in each low frequency cycle (and many more than are shown in FIG. 2) corresponds to a separate velocity in the duct 13. The low frequency cyclic nature of the signal is proportional to changes in blood flow caused, for example, by cardiac and respiratory action.

Having obtained a signal having component portions representative of the various velocities in the vessel 13 it is now necessary to count the number of such velocities in unit time in order to provide a measure of the cross-sectional area of the vessel. First, however, the low frequency signal due to cyclic variations in blood flow has to be removed and this is carried out by a capacitor 20, typically of value 0.1 microfarads. The capacitor 20 is coupled to the input of another frequency-to-voltage converter 21 which is preferably another PLL of the type mentioned above. The voltage produced by this converter is related to the number of component portions present in the output from the PLL 16 and therefore representative of the number of velocities present in the duct 13.

It has been found that the output of PLL 16 is not linearly related to the instantaneous cross-sectional area of the vessel 13 and for this reason a multiplier circuit 22 which provides signal squaring is inserted to provide an output signal linearly proportional to vessel area. A suitable circuit is the "Analog Devices", 4-quad multiplier type AD 532. It will be appreciated that the type of circuit used to linearize the output of the PLL to cross-sectional area depends on the characteristic of the converter 21.

The apparatus of FIG. 1 does not, in its present form, give an absolute measure of cross-sectional area but it does provide a signal which varies as the cross-sectional area of the vessel 13 varies. The device of FIG. 1 can be used for comparing cross-sectional areas of different blood vessels or of different portions of the same blood vessel but such comparisons cannot be made, in general, using different probes. Absolute measurements can, however, be obtained by calibrating the apparatus of FIG. 1 against known cross-sectional areas.

It will be realized that the invention can be put into practice in many other ways. For example different types of frequency-to-voltage converters may be used and the areas of ducts containing other fluids than blood can, of course, be measured, the only limitation being that the fluid in the duct gives rise to a large number of different Doppler signals. The fluid can therefore be a liquid such as water which normally contains dissolved air bubbles sufficient to provide the required Doppler signals, a "fluid" comprising solid particles passing along a duct or a gas provided it meets the limitation mentioned above.

In order to provide an indication of volume flow rate the cross-sectional area of the duct must be multiplied by a signal representative of mean velocity of fluid in the duct. Apparatus for this purpose is described by Sainz et al in Ultrasonics 14, 128 (1976) "Phase locked loop techniques applied to ultrasonic Doppler system processing". Briefly, a velocity signal can be derived from a further PLL 23 connected to the output of the amplifier 14. Much the same sort of output is produced as is shown in FIG. 2 except that the maxima and minima representing different frequencies have durations which depend on the amplitude of the receive signal. A mean detector 24 establishes the mean of the waveform from the PLL 23 and therefore provides an indication of the mean Doppler frequency (proportional to mean velocity) for a multiplier 25 which multiplies the linearizer output (proportional to cross-sectional area) by the mean velocity to provide a signal representative of volume flow rate.

We claim:

1. Apparatus for measuring the cross-sectional area of a duct containing a fluid, comprising
   means for deriving a plurality of velocity signals, each having a frequency which corresponds to a respective velocity of fluid in a duct, the number of velocity signals depending on the number of different velocities currently present in the duct,
   a frequency-to-voltage converter coupled to receive the velocity signals, and
   means responsive to the varying output of the said converter to provide a signal representative of duct cross-sectional area.

2. Apparatus according to claim 1 for additionally measuring volume flow rate, comprising
   means for deriving a signal representative of mean fluid velocity in the duct, and
   means for forming a signal representative of the product of the signal representative of duct cross-sectional area and the signal representative of mean fluid velocity in the duct.

3. Apparatus according claim 1 wherein
   an amplitude limiter circuit is coupled to the input of said converter.

4. Apparatus according to claim 1 wherein
   the means responsive to the varying output of said converter comprises a further frequency-to-voltage converter.

5. Apparatus according to claim 4 including
   means coupled between the two converters for removing low frequency signals at the input of the further frequency-to-voltage converter.

6. Apparatus according to claim 4 including
   a linearizer circuit coupled to the output of the further frequency-to-voltage converter.

7. Apparatus according to claim 4 wherein
   at least one of the frequency-to-voltage converters comprises a phase-locked loop circuit.

8. Apparatus according to claim 6 wherein
   the further frequency-to-voltage converter comprises a phase-locked loop and the linearizer circuit is based on a square law characteristic.

9. Apparatus according to claim 1 wherein the means for deriving a plurality of velocity signals comprises
   an oscillator coupled to an ultrasound transmission transducer, and
   an ultrasound transmission receiver which derives a plurality of signals each having a frequency dependent on a respective fluid velocity in the duct.